(12) United States Patent
Crispin et al.

(10) Patent No.: US 12,141,342 B2
(45) Date of Patent: Nov. 12, 2024

(54) BIOFEEDBACK METHOD OF MODULATING DIGITAL CONTENT TO INVOKE GREATER PUPIL RADIUS RESPONSE

(71) Applicant: APPLE INC., Cupertino, CA (US)

(72) Inventors: Sterling R. Crispin, Santa Cruz, CA (US); Izzet B. Yildiz, Sunnyvale, CA (US); Grant H. Mulliken, San Jose, CA (US)

(73) Assignee: Apple Inc., Cupertino, CA (US)

( * ) Notice: Subject to any disclaimer, the term of this patent is extended or adjusted under 35 U.S.C. 154(b) by 287 days.

(21) Appl. No.: 17/381,228

(22) Filed: Jul. 21, 2021

(65) Prior Publication Data

US 2021/0349536 A1 Nov. 11, 2021

Related U.S. Application Data

(63) Continuation of application No. PCT/US2020/014706, filed on Jan. 23, 2020.

(Continued)

(51) Int. Cl.
*G06N 5/04* (2023.01)
*G06F 3/01* (2006.01)
(Continued)

(52) U.S. Cl.
CPC .............. *G06F 3/013* (2013.01); *G06N 5/04* (2013.01); *G06N 20/00* (2019.01); *G06T 7/62* (2017.01);
(Continued)

(58) Field of Classification Search
CPC .......... G06F 3/011; G06F 3/013; F06V 40/19; G06T 7/62; G06N 20/00; G06N 5/04
See application file for complete search history.

(56) References Cited

U.S. PATENT DOCUMENTS 7,744,216 B1  6/2010  Uhlhorn
9,734,633 B2  8/2017  Bennett et al.
(Continued)

FOREIGN PATENT DOCUMENTS

WO   97/19371 A2   5/1997
WO   2013/138632 A1   9/2013
(Continued)

OTHER PUBLICATIONS

European Patent Office, Examination Report (Communication pursuant to Article 94(3) EPC), European Patent Application No. 20709792.4, 8 pages, Feb. 16, 2023.
(Continued)

*Primary Examiner* — Olga V Merkoulova
(74) *Attorney, Agent, or Firm* — Thompson Hine LLP

(57) ABSTRACT

One exemplary implementation displays a visual characteristic associated with an object on a display of a device and utilizes a sensor of the device to obtain physiological data associated with a pupillary response of a user to the visual characteristic. The device adjusts the visual characteristic based on the obtained physiological data to enhance pupillary responses of the user to the object and displays the adjusted visual characteristic to the user. For example, the adjusted visual characteristic may be selected based on previously identified pupillary responses of the user to particular visual characteristics.

18 Claims, 9 Drawing Sheets

Related U.S. Application Data

(60) Provisional application No. 62/799,914, filed on Feb. 1, 2019.

(51) Int. Cl.
  *G06N 20/00* (2019.01)
  *G06T 7/62* (2017.01)

(52) U.S. Cl.
  CPC .............. *G06T 2207/20081* (2013.01); *G06T 2207/30201* (2013.01)

(56) References Cited

U.S. PATENT DOCUMENTS

| | | | |
|---|---|---|---|
| 9,996,973 B2 | 6/2018 | Shuster et al. | |
| 10,810,773 B2* | 10/2020 | Yildiz | G06V 40/19 |
| 10,921,605 B2* | 2/2021 | Reyes | G10L 25/18 |
| 10,942,565 B2* | 3/2021 | Ho | G06F 3/147 |
| 10,950,332 B2* | 3/2021 | Davey | G16H 20/70 |
| 11,119,573 B2* | 9/2021 | Bar-Zeev | G06F 3/011 |
| 11,678,014 B2* | 6/2023 | Daly | H04N 21/84 725/35 |
| 2012/0257035 A1 | 10/2012 | Larsen | |
| 2013/0243270 A1 | 9/2013 | Kamhi et al. | |
| 2014/0064578 A1 | 3/2014 | Choe | |
| 2014/0108842 A1* | 4/2014 | Frank | G06F 1/3212 713/323 |
| 2015/0254508 A1 | 9/2015 | Kimura et al. | |
| 2015/0332166 A1 | 11/2015 | Ferens et al. | |
| 2016/0225012 A1 | 8/2016 | Ha et al. | |
| 2017/0255766 A1* | 9/2017 | Kaehler | G06V 40/19 |
| 2017/0293356 A1* | 10/2017 | Khaderi | G02B 27/0172 |
| 2018/0286070 A1* | 10/2018 | Benedetto | G06T 7/62 |
| 2019/0265785 A1* | 8/2019 | Ho | G06F 3/013 |
| 2019/0295699 A1* | 9/2019 | Davey | G06F 13/4221 |
| 2020/0041803 A1* | 2/2020 | Reyes | G06V 40/10 |
| 2020/0103967 A1* | 4/2020 | Bar-Zeev | G06V 40/174 |
| 2021/0191512 A1* | 6/2021 | Ho | G09G 5/10 |
| 2021/0365116 A1* | 11/2021 | Bar-Zeev | G06F 3/015 |
| 2023/0284962 A1* | 9/2023 | Dam | G16H 50/20 |

FOREIGN PATENT DOCUMENTS

| | | |
|---|---|---|
| WO | 2015/041668 A1 | 3/2015 |
| WO | 2016/142933 A1 | 9/2016 |

OTHER PUBLICATIONS

European Patent Office (ISA/EP), International Search Report and Written Opinion of the International Searching Authority, International Application No. PCT/US2020/014706, 16 pages (May 25, 2020).

Hess, E.H. et al., "Pupil Size as Related to Interest Value of Visual Stimuli," Science, vol. 132, No. 3423, pp. 349-350 (Aug. 5, 1960).

European Patent Office, Examination Report (Communication pursuant to Article 94(3) EPC) issued Jan. 31, 2024, which pertains to European Patent Application No. 20709792.4. 8 pgs.

China National Intellectual Property Administration, Chinese Office Action issued Feb. 21, 2024 [English Translation], which pertains to Chinese Patent Application No. 202080011940.4. 10 pgs.

* cited by examiner

BIOFEEDBACK METHOD OF MODULATING DIGITAL CONTENT TO INVOKE GREATER PUPIL RADIUS RESPONSE

TECHNICAL FIELD

The present disclosure generally relates to displaying objects with electronic devices, and in particular, to systems, methods, and devices for adjusting visual characteristics associated with objects to enhance a pupillary response of a user.

BACKGROUND

Electronic devices have different capabilities with respect to viewing and interacting with electronic content. A variety of input mechanisms have been incorporated into a variety of user devices to provide functionality and user interaction (e.g., keyboards, mice, touchscreens, buttons, microphones for voice commands, optical sensors, etc.). For example, touch screens have been incorporated into mobile phones (e.g., smartphones), tablet computers, wearable devices (e.g., watches, glasses, head-mounted devices, etc.), and other computing devices, allowing software developers to create engaging software applications ("apps") for entertainment, productivity, health, and the like. In some instances, touch screens work in conjunction with a variety of other input mechanisms for interacting with a device (e.g., optical sensors, buttons, microphones for voice commands, etc.).

Many devices, however, can have limited device interaction and control capabilities due to device size constraints, display size constraints, operational constraints, etc. For example, small or thin user devices can have a limited number of physical buttons for receiving user input. Similarly, small user devices can have touchscreens with limited space for providing virtual buttons or other virtual user interface elements. In addition, some devices can have buttons or other interactive elements that are unnatural, cumbersome, or uncomfortable to use in certain positions or in certain operating conditions. For example, it may be cumbersome to interact with a device using both hands (e.g., holding a device in one hand while engaging interface elements with the other). In another example, it may be difficult to press small buttons or engage touchscreen functions while a user's hands are otherwise occupied or unavailable (e.g., when wearing gloves, carrying groceries, holding a child's hand, driving, etc.). In still other examples, device interaction can be limited in a variety of other ways.

SUMMARY

Various implementations disclosed herein include devices, systems, and methods that adjust a visual characteristic (e.g., hue, saturation, size, shape, spatial frequency, motion, highlighting, etc.) associated with an object (e.g., button, UI icon, etc.) to enhance pupillary responses of a user to the display of the object. The device (e.g., a handheld, laptop, desktop, or head-mounted device (HMD)) displays, on a display, the visual characteristic associated with the object to the user and obtains, with a sensor, physiological data (e.g., pupil dilation) associated with a response of the user to the visual characteristic. Based on the obtained physiological data, the device adjusts the visual characteristic to enhance the pupillary response of the user to the object.

In some implementations, the device evaluates physiological responses of a user expecting interface feedback following an interaction with the object in a user interface. The physiological responses may be associated with the user expecting the interface feedback using multiple alternative interface feedback characteristics. In one example, it is desirable to predict a user's intention to select a button prior to the user selecting the button based on the user's pupil dilation when the user intends to select the button. To facilitate such predictions, it may be desirable to configure the button, including feedback associated with selection of the button, to provide significant or optimal pre-selection pupil dilation change, e.g., determining that the user's preselection pupil dilation is good or optimal when the user intends to make the selection and expects certain feedback after the selection. To do so, the device may evaluate various alternative feedback characteristics (e.g., which of multiple colors a button should change to following a user's click of the button) to identify characteristics of the feedback as suitable or optimal with respect to pre-selection pupil dilation. The device may assess how much a user's eye dilates before he clicks an object when the user expects each interface feedback characteristic (e.g. the object turning pink after being clicked, the object turning orange after being clicked, etc.). In some implementations, the device then selects an interface feedback characteristic of the alternative interface feedback characteristics based on evaluating the physiological data. For example, the device may select pink as the ideal interface feedback characteristic based on determining that the user's eye dilates more when expecting the object to turn pink than when expecting the object to turn orange.

Once an object characteristic has been selected, the characteristic can be applied to facilitate intention detection (e.g., detecting that the user intends to select a button before the user selects the button based on the user's eye dilation). For example, in some implementations, the device displays the object so that selection of the displayed object provides the interface feedback using the selected interface feedback characteristic. For example, following training, the object may be displayed in an application using the pink interface feedback. The user of the interface will observe the pink interface feedback as the user uses the user interface and selects the object. Over one or more occurrences of the feedback, the user will come to expect the pink interface feedback and will generally come to exhibit the pre-selection pupil dilation associated with expecting the pink interface feedback. Thus, in some implementations, the device obtains a physiological response such as pupil dilation to the displayed object prior to a selection of the object and determines, based on the obtained physiological response, an intention of the user to interact with the object. Based on the determined intention of the user to interact with the object, the device may initiate interaction with (e.g., selection of) the object. In this example, the device is able to detect the intention of the user to select the object before the user selects the object based on the user's physiological response (e.g., pupil dilation). Moreover, because the object was intelligently configured to provide a suitable or optimal physiological response, the device may be able to identify such intentions more accurately than it otherwise would (e.g., the predictions of the user's intention to select a button may be more accurate because the user interface feedback is pink rather than orange).

In some implementations, the device adjusts the visual characteristic by obtaining pupil dilation data corresponding to multiple variations of the visual characteristic (e.g., red highlighting, blue highlighting, and green highlighting) and then selects a variation of the visual characteristic based on the pupil dilation data. As used herein, the phrase "optimized" refers generally to the visual characteristic being selected, for example, by selecting a particular variant of the visual characteristic, in any way that is beneficial with respect at least one other variant of the visual characteristic. For example, the device may select green highlighting for the optimized visual characteristic based on a determination from the pupil dilation data that the user's eye responds better to green than to red. Moreover, based on determining that the user responds better to green, the device may then adjust the visual characteristic and display the object with a green highlighting. In some implementations, the device accounts for exogenous signals corresponding to pupil diameter changes in the pupil dilation data resulting from ambient light changes, chromatic changes, accommodation of the eye, content lighting changes, cyclical pupil dilations, a change in ambient noise, a change in motion of the device, a luminance of the scene, a cognitive load, or a user caffeine intake.

In some implementations, the device obtains physiological data (e.g., pupillary data) associated with the user's response to the display of an adjusted visual characteristic and determines an intention of the user to interact with the object based on the obtained physiological data (e.g., detected pupil dilation pattern). In some implementations, the device may identify a correlation between a change in the user's physiological data and an expectation of the user that an particular visual characteristic will be displayed. For example, determining the intention of the user to select an object may include identifying the expectation of the user that feedback to the selection will have an adjusted visual characteristic. Moreover, in some implementations, determining the intention of the user includes applying a machine learning technique trained to identify patterns in physiological data corresponding to user intentions or user expectations. In some implementations, detecting the pupil dilation pattern may include accounting for exogenous signals corresponding to pupil diameter changes in the pupil dilation data resulting from ambient light changes, chromatic changes, accommodation of the eye, content lighting changes, cyclical pupil dilations, a change in ambient noise, a change in motion of the device, a luminance of the scene, a cognitive load, or a user caffeine intake.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1:
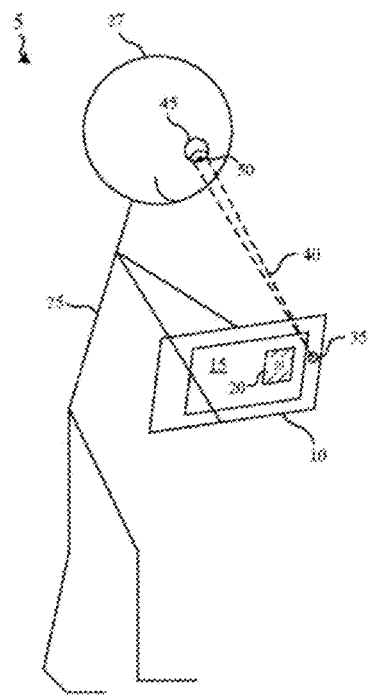
FIG. 1 illustrates a device displaying an object and obtaining physiological data from a user according to some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

FIG. 1 illustrates a real-world environment 5 including a device 10 with a display 15. In some implementations, the device 10 displays an object 20 to a user 25, and a visual characteristic 30 is associated with the object 20. For example, the object 20 may be a button, a user interface icon, a text box, a graphic, etc. In some implementations, the visual characteristic 30 associated with the object 20 includes visual characteristics such as hue, saturation, size, shape, spatial frequency, motion, highlighting, etc. For example, the object 20 may be displayed with a visual characteristic 30 of green highlighting covering or surrounding the object 20.

The device 10 obtains physiological data (e.g., pupillary data) from the user 25 via a sensor 35. While this example and other examples discussed herein illustrate a single device 10 in a real-world environment 5, the techniques disclosed herein are applicable to multiple devices as well as to other real world environments. For example, the functions of device 10 may be performed by multiple devices.

In some implementations, as illustrated in FIG. 1, the device 10 is a handheld electronic device (e.g., a smartphone or a tablet). In some implementations the device 10 is a laptop computer or a desktop computer. In some implementations, the device 10 has a touchpad and, in some implementations, the device 10 has a touch-sensitive display (also known as a "touch screen" or "touch screen display"). In some implementations, the device 10 is a wearable head mounted display (HMD).

In some implementations, the device 10 includes an eye tracking system for detecting eye position and eye movements. For example, an eye tracking system may include one or more infrared (IR) light-emitting diodes (LEDs), an eye tracking camera (e.g., near-IR (NIR) camera), and an illumination source (e.g., an NIR light source) that emits light (e.g., NIR light) towards the eyes of the user 25. Moreover, the illumination source of the device 10 may emit NIR light to illuminate the eyes of the user 25 and the NIR camera may capture images of the eyes of the user 25. In some implementations, images captured by the eye tracking system may be analyzed to detect position and movements of the eyes of the user 25, or to detect other information about the eyes such as pupil dilation or pupil diameter. Moreover, the point of gaze estimated from the eye tracking images may enable gaze-based interaction with content shown on the near-eye display of the device 10.

In some implementations, the device 10 has a graphical user interface (GUI), one or more processors, memory and one or more modules, programs or sets of instructions stored in the memory for performing multiple functions. In some implementations, the user 25 interacts with the GUI through finger contacts and gestures on the touch-sensitive surface. In some implementations, the functions include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions may be included in a computer readable storage medium or other computer program product configured for execution by one or more processors.

In some implementations, the device 10 employs various physiological sensor, detection, or measurement systems. Detected physiological data may include, but is not limited to, electroencephalography (EEG), electrocardiography (ECG), electromyography (EMG), functional near infrared spectroscopy signal (fNIRS), blood pressure, skin conductance, or pupillary response. Moreover, the device 10 may simultaneously detect multiple forms of physiological data in order to benefit from synchronous acquisition of physiological data. Moreover, in some implementations, the physiological data represents involuntary data, e.g., responses that are not under conscious control. For example, a pupillary response may represent an involuntary movement.

In some implementations, one or both eyes 45 of the user 25, including one or both pupils 50 of the user 25 present physiological data in the form of a pupillary response. The pupillary response of the user 25 results in a varying of the size or diameter of the pupil 50, via the optic and oculomotor cranial nerve. For example, the pupillary response may include a constriction response (miosis), e.g., a narrowing of the pupil, or a dilation response (mydriasis), e.g., a widening of the pupil. In some implementations, the device 10 may detect patterns of physiological data representing a time-varying pupil diameter.

Figure 2:
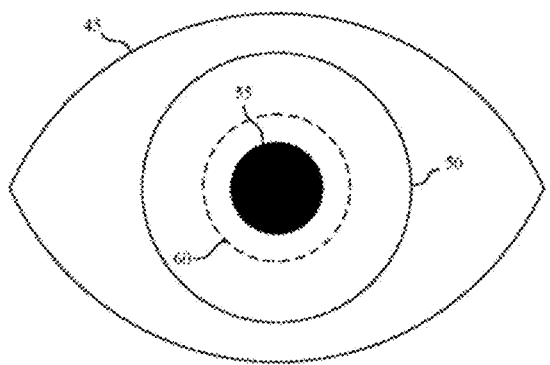
FIG. 2 illustrates a pupil of the user of FIG. 1 in which the diameter of the pupil varies with time in accordance with some implementations.

FIG. 2 illustrates a pupil 50 of the user 25 of FIG. 1 in which the diameter of the pupil 50 varies with time. As shown in FIG. 2, a present physiological state (e.g., present pupil diameter 55) may vary in contrast to a past physiological state (e.g., past pupil diameter 60) For example, the present physiological state may include a present pupil diameter and a past physiological state may include a past pupil diameter.

The physiological data may vary in time and the device 10 may use the physiological data to measure one or both of a user's physiological response to the visual characteristic 30 or the user's intention to interact with the object 20. For example, when presented with an object 20, such as a list of files, by a device 10, the user 25 may select an object 20 without requiring the user 25 to complete a physical button press. In some implementations, the physiological data includes the response of a radius of the pupil 50 after the user 25 glances at the object 20, measured via eye-tracking technology.

The visual characteristic 30 associated with the object 20 may be adjusted to drive or enhance the physiological response of the user 25. Such adjustment can be implemented for an object during a particular user interaction with the object or during future interactions with the object. For example, object 20 could be highlighted in red, then green, then yellow as the user is looking at it, and based on detecting that the user responds best to green, the object can remain green for the remainder of the interaction. In another example, based on determining that the user reacts to green, the visual characteristic may be varied over time accordingly. For example, green highlighting around the object 20 could be gradually adjusted during the course of the user interaction to continually elicit an ever greater response. In some implementations, an object is animated to darken, brighten or change in luminance contrast, shift in hue, shift in spatial pattern or move in some way that would drive modulation of the pupil 50. Furthermore, in some implementations, the visual characteristic 30 associated with the object 20 is changed, e.g., prior to execution of a movement or a 'moment' of intention, to build an expectation in the user that interaction will result in change (e.g., animation) of the visual characteristic 30 associated with the object 20.

Figure 3:
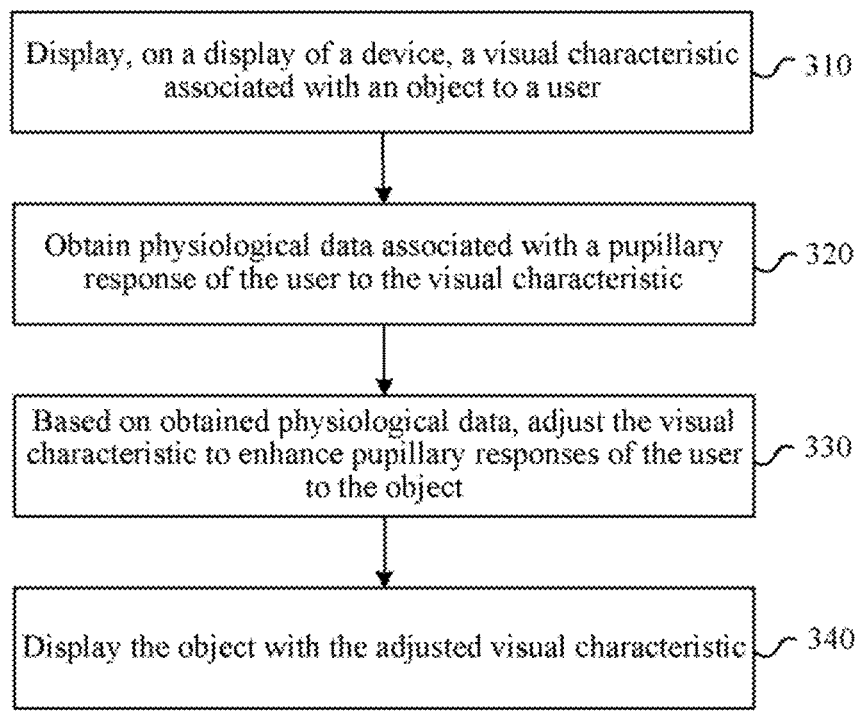
FIG. 3 is a flowchart representation of a method for adjusting visual characteristics to enhance a pupillary response of a user.

FIG. 3, in accordance with some implementations, is a flowchart representation of a method 300 for adjusting visual characteristics associated with objects (e.g., object 20) to enhance a pupillary response of a user (e.g., user 25). In some implementations, the method 300 is performed by one or more devices (e.g., device 10). The method 300 can be performed at a mobile device, HMD, desktop, laptop, or server device. The method 300 can be performed on an HMD that has a screen for displaying 3D images or a screen for viewing stereoscopic images. In some implementations, the method 300 is performed by processing logic, including hardware, firmware, software, or a combination thereof. In some implementations, the method 300 is performed by a processor executing code stored in a non-transitory computer-readable medium (e.g., a memory).

At block 310, the method 300 displays, on a display of a device, a visual characteristic associated with an object to a user. In some implementations, the object is a button, a user interface icon, a text box, or a graphic. Moreover, in some implementations, the visual characteristic associated with the object is hue, saturation, size, shape, spatial frequency, motion, or highlighting.

At block 320, the method 300 obtains physiological data associated with a pupillary response of the user to the visual characteristic displayed at block 310. In some implementations, the diameter of the pupil is measured over a period of time. In some implementations, the method 300 performs a training function by presenting the user with various visual characteristics and, respectively, recording the physiological data associated with the pupillary responses to the various visual characteristics. Accordingly, the method 300 may "learn" a particular variation of the visual characteristic to which the user's pupil best responds. In some implementations, the method 300 accounts for any exogenous signals that may affect the pupillary response. For example, increased ambient light may result in an exogenous signal affecting pupillary response.

At block 330, the method 300 adjusts the visual characteristic based on the physiological data obtained at block 320 to enhance pupillary responses of the user to the object. In some implementations, the visual characteristic is changed to provide an increased pupillary response. For example, the visual characteristic may include a highlighting of a particular color; adjustment of the visual characteristic may include changing the color of the highlighting to a color determined to, in relation to the pupillary response to the original color of the visual characteristic, elicit an enhanced pupillary response.

At block 340, the method 300 displays the object with the enhanced visual characteristic. In some implementations, the method 300 identifies an interest of the user in the object based on detecting a pattern in the obtained physiological data. In some implementations, the current interest on intent is confirmed based on the user's pupillary response to the enhanced visual characteristic.

Figure 4:
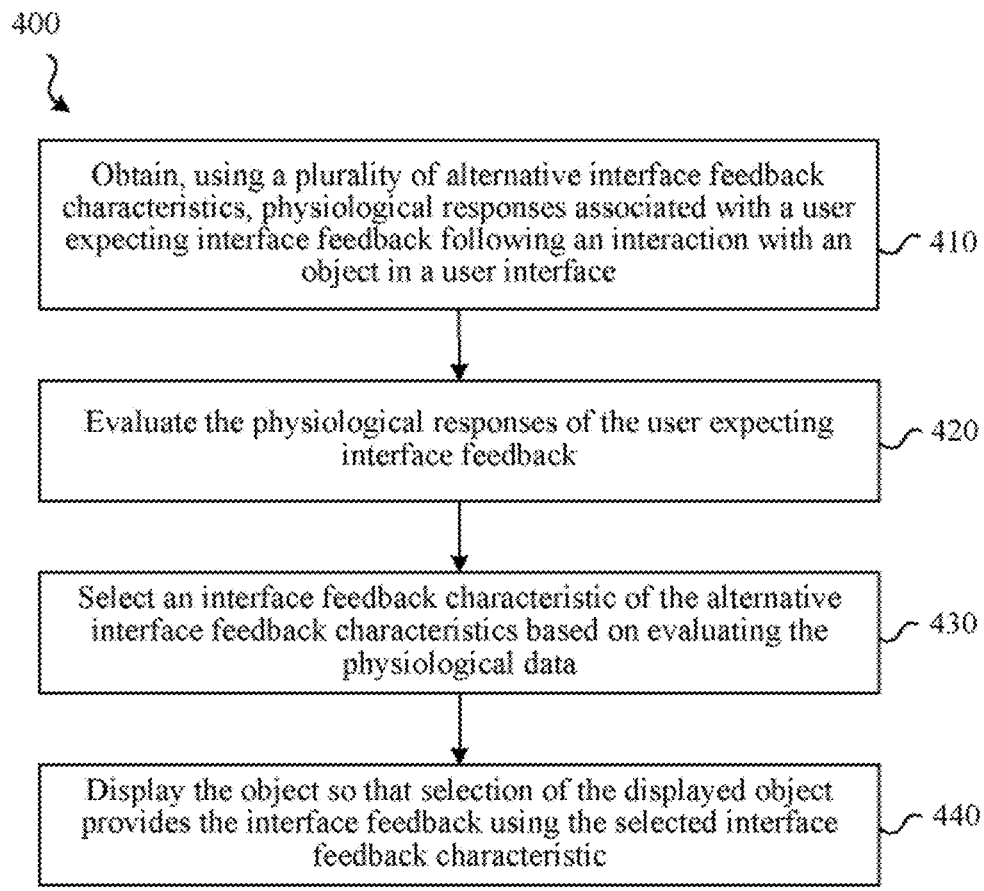
FIG. 4 is a flowchart representation of a method for selecting and displaying interface feedback characteristics to enhance physiological responses associated with a user expecting the selected interface feedback characteristics.

FIG. 4, in accordance with some implementations, is a flowchart representation of a method 400 for selecting and displaying interface feedback characteristics to enhance physiological responses associated with a user expecting the selected interface feedback characteristics. In some implementations, the method 400 is performed by one or more devices. The method 400 can be performed at a mobile device, HMD, desktop, laptop, or server device. The method 400 can be performed on an HMD that has a screen for displaying 3D images or a screen for viewing stereoscopic images. In some implementations, the method 400 is performed by processing logic, including hardware, firmware, software, or a combination thereof. In some implementations, the method 400 is performed by a processor executing code stored in a non-transitory computer-readable medium (e.g., a memory).

At block 410, the method 400 obtains, using a plurality of alternative interface feedback characteristics, physiological responses associated with a user expecting interface feedback following an interaction with an object in a user interface. In some implementations, the method 400 presents the user with a particular interface feedback multiple times and, in some implementations, a user may be repeatedly presented with a particular interface feedback until the user's physiological response to presentation of the object shows that the user expects the particular interface feedback will occur after interacting with the object. For example, a user may be presented with a button and may exhibit a baseline or "naive" pupillary diameter of 2 mm. After interacting with the object, the user may be surprised by an interface feedback of a colorful change in color of the button (e.g., color changing from blue to pink). After interacting with the object some number of times (e.g., a statistically significant sampling of physiological data or until the physiological data has stabilized), the user may expect the interface feedback and may exhibit an excited pupillary dimeter of 4 mm upon being presented with the button, e.g., when the user intends to interact with the button but prior to interacting with the button. Moreover, in some implementations, the user may be presented with additional interface feedback characteristics so that the obtained physiological responses of the user reflect the user's response to a number of different interface feedback characteristics (e.g., change of color to different colors, highlighting, audio feedback, etc.).

At block 420, the method 400 evaluates the physiological responses of the user expecting interface feedback obtained at block 410. In some implementations, the method 400 assesses the physiological responses based on each of the different interface feedback characteristics or based on the number of obtained physiological responses for each of the different feedback characteristics. For example, the method 400 may assess how much a user's eye dilates before clicking an object when the user expects the object to turn pink after being clicked and the method 400 may assess how much the user's eye dilates before he clicks the object when the user expects the object to turn orange after being clicked. Moreover, the method 400 may assess how quickly the user is conditioned to expect each feedback characteristic based on one or more factors (e.g., number of collected physiological responses required for a stable response).

At block 430, the method 400 selects an interface feedback characteristic of the alternative interface feedback characteristics based on the evaluation of the physiological data performed at block 420. In some implementations, the method 400 seeks to maximize a difference between the user's naive physiological response to the presentation of the object as compared with the user's physiological response to the presentation of the object when the user expects the interface feedback. For example, the method 400 may assess how much a user's eye dilates, in relation to the user's baseline or naive pupillary diameter, before the user clicks an object when the user expects the object to turn pink after being clicked and may compare the pink color change assessment to an assessment of how much the user's eye dilates before clicking the object when the user expects the object to turn orange after being clicked, etc. Moreover, the method 400 may determine that the pink color change assessment may elicit the greatest change in pupillary diameter between the user's naive/baseline pupillary diameter and the user's pupillary diameter when the user expects the object to turn pink. Thus, the method 400 may select pink as an ideal interface feedback characteristic.

At block 440, the method 400 displays the object so that selection of the displayed object provides the interface feedback using the interface feedback characteristic selected at block 430. For example, following training of the user or device, an object may be displayed in an application using the pink interface feedback. In some implementations, prior to providing the interface feedback using the selected interface feedback characteristic, the method 400 obtains a physiological response of the user to the displayed object prior to a selection of the object, determines an intention of the user to interact with the object based on the obtained physiological response, and initiates the interaction with (e.g., selection of) the object based on determining the intention of the user to interact with the object.

Figure 5:
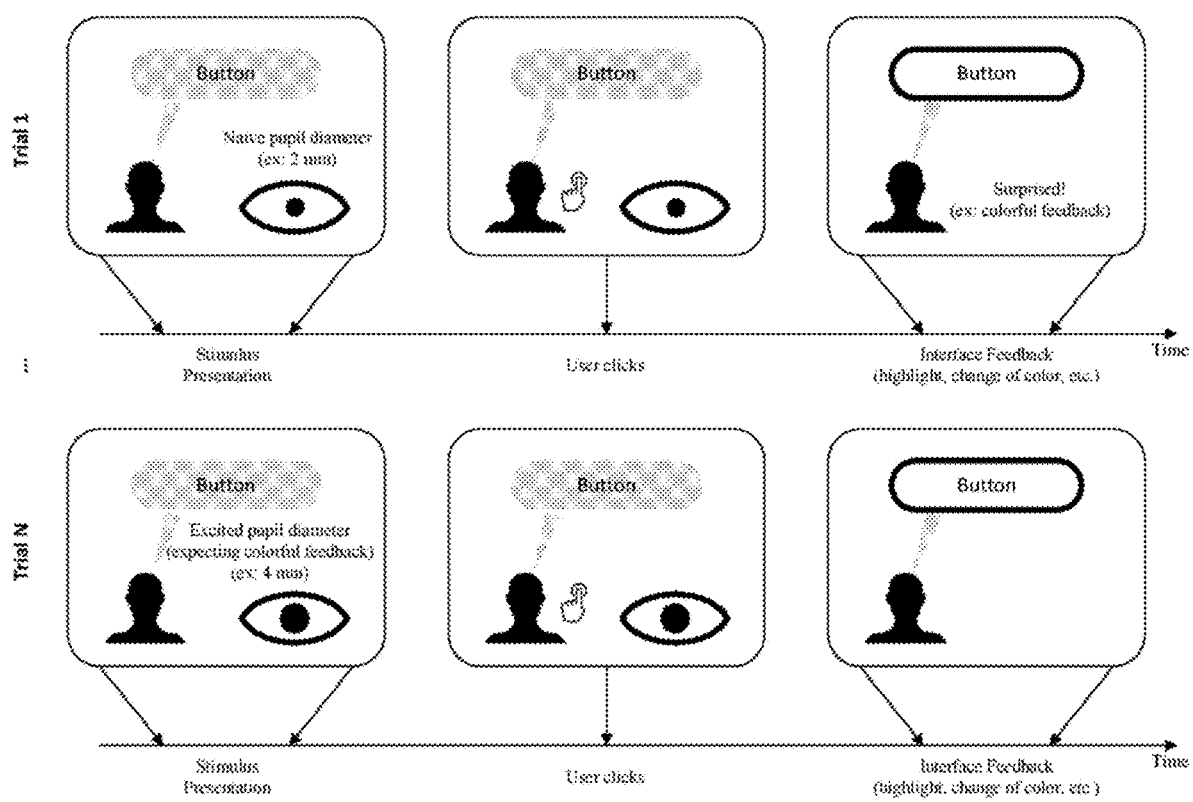
FIG. 5 is a chart illustrating a training process where multiple alternative interface feedbacks are assessed to select an interface feedback.

FIG. 5 illustrates a training process where multiple alternative interface feedbacks are assessed to select an interface feedback. In some implementations, the interface feedback is selected based on an evaluation of the physiological response of the user to the presentation of an object or stimulus (e.g., a button) when the user expects to be presented with the interface feedback upon interacting with the object or stimulus (e.g., clicking the button). For example, the training process may involve, for each alternative interface feedback, performing a series of trials (e.g., Trial 1 through Trial N) where the device effectively learns how well the expected pupil diameter of the user responds to a post-click interface feedback.

In some implementations, a training process including multiple trials for each interface feedback condition is performed. For example, the training process may include identifying an ideal color to change the button after the user clicks it. Thus, from Trial 1 to Trial N, the interface feedback condition of the button may be a color change from an initial color (e.g., solid blue) to another color (e.g., solid pink), and in another set of trials (e.g., 10 trials). the interface feedback condition may include the button changing from the initial color to a different color (e.g., solid orange). As the user interacts with (e.g., clicks) the object (e.g., the button) in each trial (e.g., Trial 1 through Trial N), the user repeatedly experiences the interface feedback condition and develops an expectation of being presented with the interface feedback condition.

In some implementations, over the course of the trials, the device determines a physiological response of the user prior to interacting with the object when the user expects to be presented with the interface feedback after interacting with the object. For example, the training process may form a correlation between the obtained physiological data (e.g. pupil diameter) and an expectation of a visual characteristic (e.g., colorful feedback such as highlighting or change of color) associated with an object (e.g., a stimulus such as a button). In some implementations, the user is conditioned to expect a change in the visual characteristic associated with the object and a change in physiological state of the user is detected by the device based on the conditioned expectation.

As shown in the example of FIG. 5, a first series of trials may present a user with a blue button that changes to pink after the user clicks the button. Prior to clicking the button in Trial 1, the user may present a baseline physiological characteristic (e.g., naïve pupil diameter of 2 mm). As the user performs additional trials, the user may develop an expectation of the interface feedback condition and, upon presentation of the object (e.g., the button), the user may present a physiological response that reflects the expectation of the interface feedback condition (e.g., an excited or expected pupil diameter). For example, in Trial N, the user may present an excited pupil diameter of 4 mm prior to interacting with the button due to the expectation of the user that the button will change pink after clicking it.

Thus, in some implementations, the device conditions the user to present heightened physiological responses in anticipation of the visual characteristic. As shown in Trial N of FIG. 5, after N number of repetitions, the user has been conditioned to expect the visual characteristic and, upon being presented with the stimulus, the user exhibits a heightened physiological response (e.g., pupil diameter of 4 mm) in anticipation of interacting with the stimulus.

In some implementations, additional series of trials are performed in order to determine which interface feedback characteristic elicits a significant or optimal physiological characteristic response from the user in expectation of interacting with the object (e.g., prior to interacting with the object). For example, a second series of trials may be performed in which the button turns from blue to orange after the user clicks it and the system may determine that, by Trial N, the user presents a pupillary diameter of 3 mm prior to interacting with the button. In some implementations, over the course of the multiple trials, the device learns via the training process to select the ideal or optimal interface feedback (e.g., the interface feedback characteristic that elicits the strongest physiological response to presentation of the object, prior to interacting with the object). For example, by comparing the expected pupillary diameters (e.g., a pupillary diameter of 4 mm for a change from blue to pink and a pupillary diameter of 3 mm for a change from blue to orange), the device may determine to use pink highlighting for the interface feedback to elicit the greater expected pupillary diameter from the user.

Figure 6:
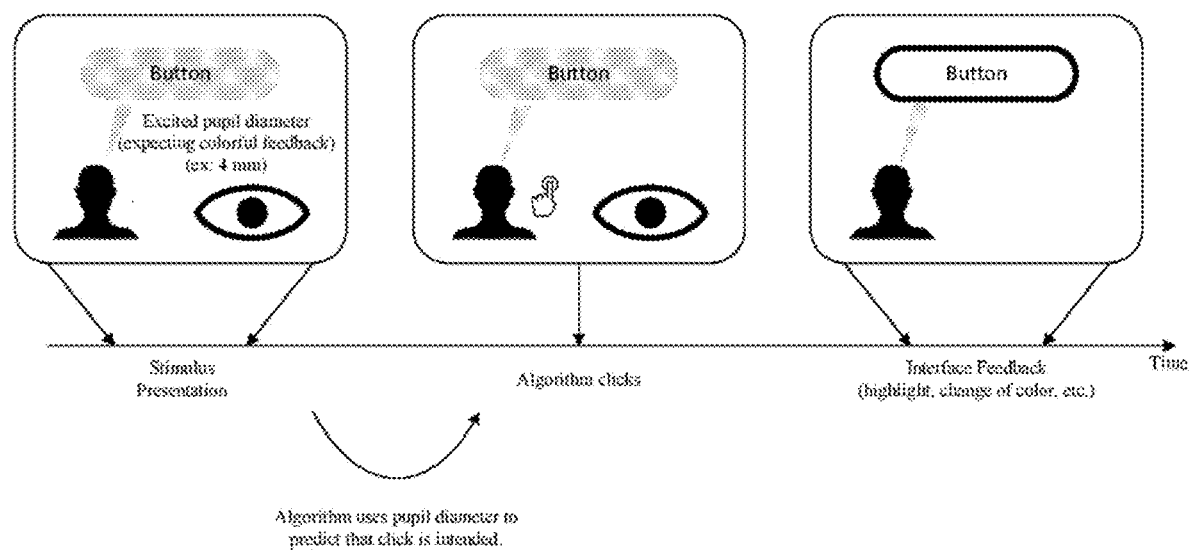
FIG. 6 is a chart illustrating an application of the interface feedback selected in FIG. 5.

FIG. 6 illustrates an application of the interface feedback selected in FIG. 5. In some implementations, by continuing to present the user with the interface feedback, the device may determine the user's intention to interact with the object based on the physiological response of the user to presentation of the object. For example, the system may identify that the user intends to interact with the object based on whether the user presents a physiological characteristic associated with the user's expectation that the interface feedback condition will take place. Thus, in some implementations, rather than physically interacting with the object, the device may perform the interaction on behalf of the user based on the user's identified expectation of the interface feedback condition.

In some implementations, when the user is using the device, the device continues to use the selected interface feedback when the user interacts with an object, and also makes a prediction that, based on a physiological response (e.g., excited pupil diameter) to a presentation of the object to the user, the user desires or intends to interact with the object (e.g., click the object). Moreover, the capability of the device to identify the predictive physiological response is enhanced by utilizing the interface feedback (e.g., the interface feedback which elicits the largest pupil diameters in expectation of the interface feedback). For example, once the interface feedback of the button changing from blue to pink is selected, it may be employed by the device so that the button changes from blue to pink after the user clicks the button; the device may then measure the pupillary dimeter of the user to predict a button click based on the expected pupillary diameter of the user.

Accordingly, by identifying physiological data associated with an expectation of a visual characteristic, the device may identify the heightened physiological state of the user upon presentation of the stimulus and predict that the user intends to interact with the stimulus. For example, the user may be conditioned to expect a change in the visual characteristic (e.g., a change of color) associated with the object 20 (e.g., a button) and may present a change in physiological states based on the expectation. Moreover, the device may automatically perform the interaction with object in response to the identified intent or expectation of the user. As another example, if a user has been conditioned to expect that a dial button on his phone turns from gray to green after being clicked, and the phone has identified that the user exhibits an excited pupillary diameter of 3 mm in expectation of the dial button turning green (e.g., prior to selecting the dial button), then the phone may use a detection of the 3 mm excited pupillary diameter to make the call and display the characteristic of the dial button turning green (e.g., without the user physically clicking the dial button).

In some implementations, the object also includes auditory properties which are adjusted to evoke larger physiological intent-like responses that are predictive of the impending stimulus change. For example, even though the object is visible, it may also have auditory properties (or other sensory properties such as tactile, olfactory, etc.) that can also change after selection (e.g., emit a sound characteristic, vibration, particular smell, etc.). Moreover, Since the object is spatially defined, spatial audio rendering is used in some implementations.

In some implementations, the device obtains physiological data from the user based on identifying typical interactions of the user with the object. For example, the device may determine that a pupillary response of the user correlates with an interaction with the object; the device may then adjust a visual characteristic of the object to enhance pupillary responses associated with future interactions with the object. Moreover, in some implementations, changing the visual characteristic after the user interacts with the object informs the physiological response of the user in subsequent interactions with the object. For example, the user may present an anticipatory physiological response associated with the change in visual characteristic prior to the visual characteristic being changed. Thus, in some implementations, the device identifies an intent of the user to interact with the object based on an anticipatory physiological response. For example, the device may adapt or train itself by capturing or storing a pupillary response of the user based on the interaction of the user with the object, including the user's response to an enhanced visual characteristic of the object, and may detect a future intention of the user to interact with the object by identifying a physiological response of the user in anticipation of display of the enhanced visual characteristic (e.g., prior to the interaction with the object).

In some implementations, an estimator or statistical learning method is used to better understand or make predictions about the physiological data (e.g., pupil diameter). For example, statistics for pupillary response data may be estimated by sampling a dataset with replacement (e.g., a bootstrap method).

Figure 7:
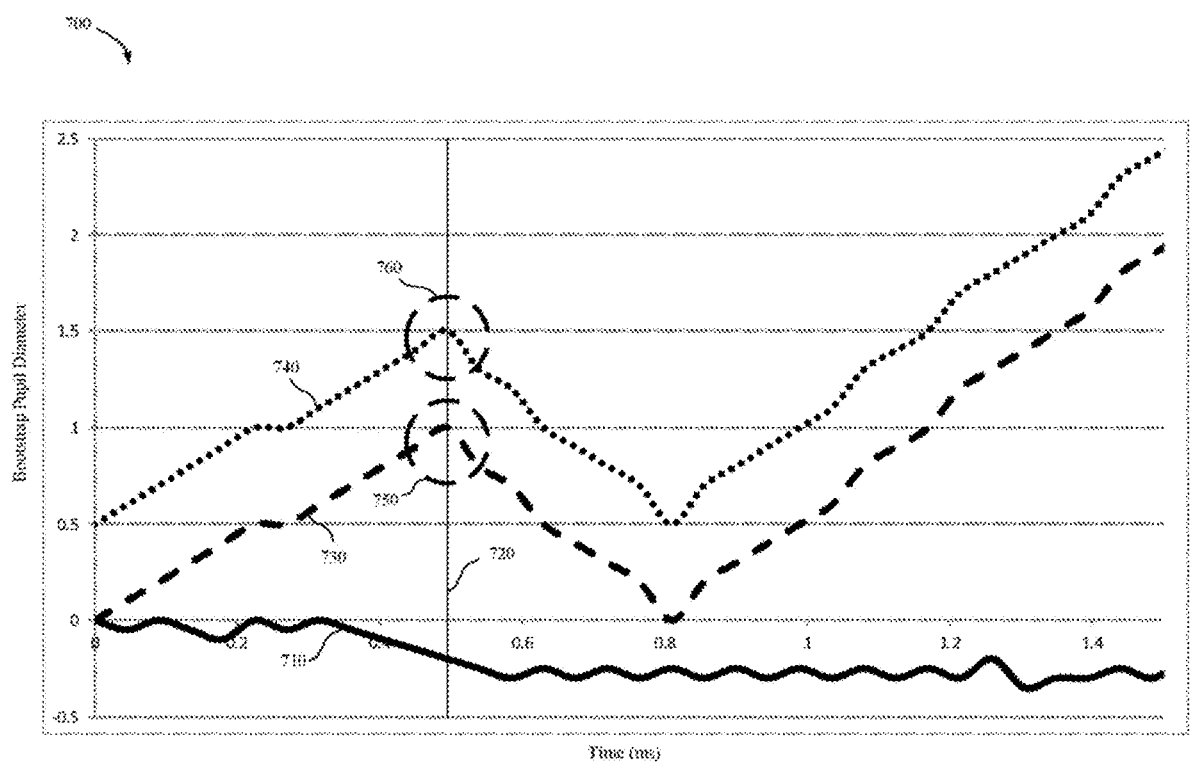
FIG. 7 is a chart illustrating obtained physiological data, including a moment of intent, over a period of time in accordance with some implementations.

FIG. 7 is a chart 700 illustrating a pupillary response over time, including a baseline time-varying pattern 710 of physiological data, e.g., a bootstrap pupil diameter (y-axis) over time (x-axis). In some implementations, the device 10 may modulate the extent by which a visual characteristic 30 associated with an object 20 is changed or adjusted with the goal of increasing the signal-to-noise ratio found in modulation of the pupil 50 at the onset of interaction. For example, an accentuated pupil signal may be thresholded or compared to a baseline pupil response (e.g., baseline time-varying pattern 710 of physiological data) by a binary classifier to detect intention towards a specific item or object.

In some implementations, feedback is varied continuously over time such that the strength of the visual characteristic 30 is modulated according to the present pupil diameter 55 and, in some implementations, the continuous feedback signal facilitates error-driven learning to improve intention control using the pupil 50. For example, a set of predefined feedback parameters could be provided as initialization or the device 10 may be trained within a particular user experience, where the predefined feedback parameters are determined to provide more significant pupil responses. Moreover, limits may be defined which keep the visual look and feel of visual characteristic 30 within an acceptable range defined by designers so the object 20 or visual characteristic 30 does not enter into an undesirable feedback loop. For example, defined limits may prevent the device 10 from maximizing pupil modulation by associating an undesirable visual characteristic 30 with the object, e.g., rapidly flashing or some other unwanted animation. In some implementations, the device 10 could be trained on many sets of user physiological data and then adapted to each user individually.

In some implementations, the device 10 also accounts for real-world environment 5 of the user 25 (e.g., visual qualities such as luminance, contrast, semantic context) in its evaluation of how much to modulate or adjust the visual characteristic 30 to enhance the physiological response (e.g., pupillary response) of the user 25 to the visual characteristic 30. As shown in FIG. 7, an illustrative time-varying pattern 730 of physiological data exhibits a peak 750 in that coincides with a moment 720 of user intent (e.g., a selection). For example, the moment 720 of user intent may coincide with a "click" made by the user 25. Likewise, FIG. 7 also includes an illustrative time-varying pattern 740 of physiological data, including a peak 760 that is indicative of a moment 720 of user intent.

Furthermore, time varying pattern 730 represents a user response to a visual characteristic 30 of a particular type (e.g., red highlighting) and time varying pattern 740 represents a user response to a visual characteristic 30 of a different type (e.g., green highlighting), such that the detected physiological data associated with time-varying pattern 740 is greater than the physiological data associated with time-varying pattern 730, e.g., the user exhibits more of a physiological response in time-varying pattern 740 than in time-varying pattern 730. For example, time varying pattern 730 may be recorded in response to a visual characteristic of a particular color (e.g., green) and time varying pattern 740 may be recording in response to a visual characteristic of a different color (e.g., red). Accordingly, different visual characteristics may elicit more distinguishing physiological responses in relation to a baseline physiological response. Time varying patterns 730 and 740 also show a time period after the moment 720 of intent where the physiological response increases. In some implementations, this increase in physiological response is based on a change, adjustment, or enhancement made to the visual characteristic 30 and, thus, the visual characteristic 30 may be used to drive an increase in the time varying pattern (e.g., time-varying pattern 730 or time-varying pattern 740) relative to the baseline response (e.g., baseline time-varying pattern 710). If it was previously determined that a user responds best to green, for example, a visual characteristic may drive an increase in the user's pupil diameter by gradually shifting from yellow to green.

Figure 8A:
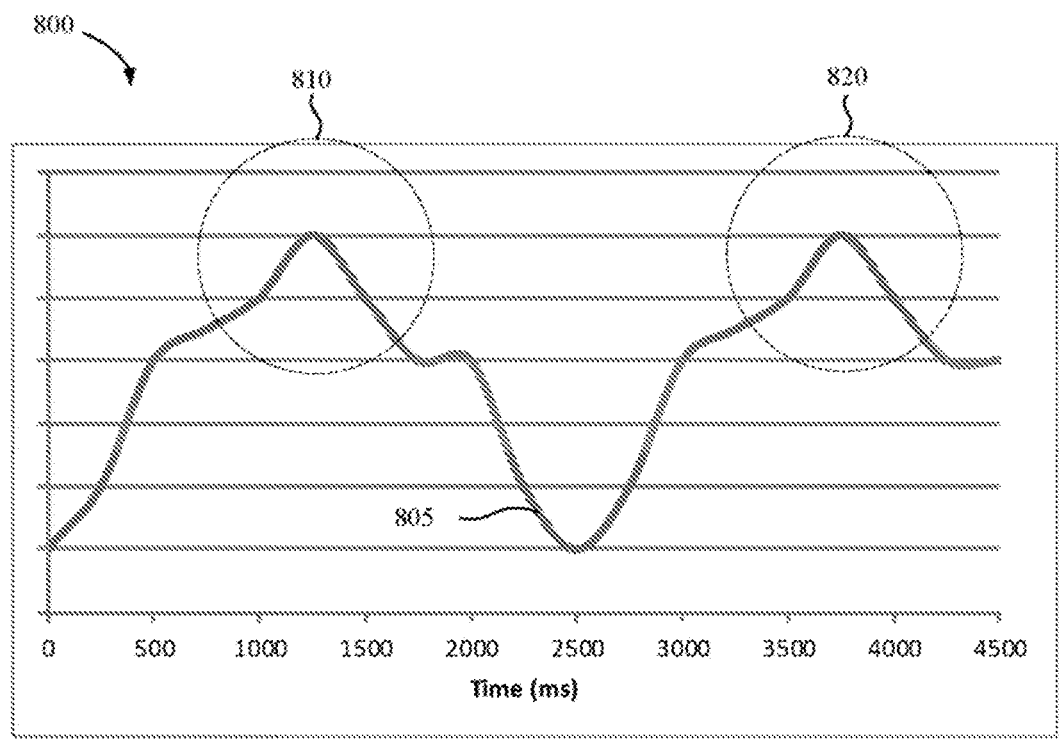
FIG. 8A is a chart illustrating detection of a pattern of physiological data in accordance with some implementations.
Figure 8B:
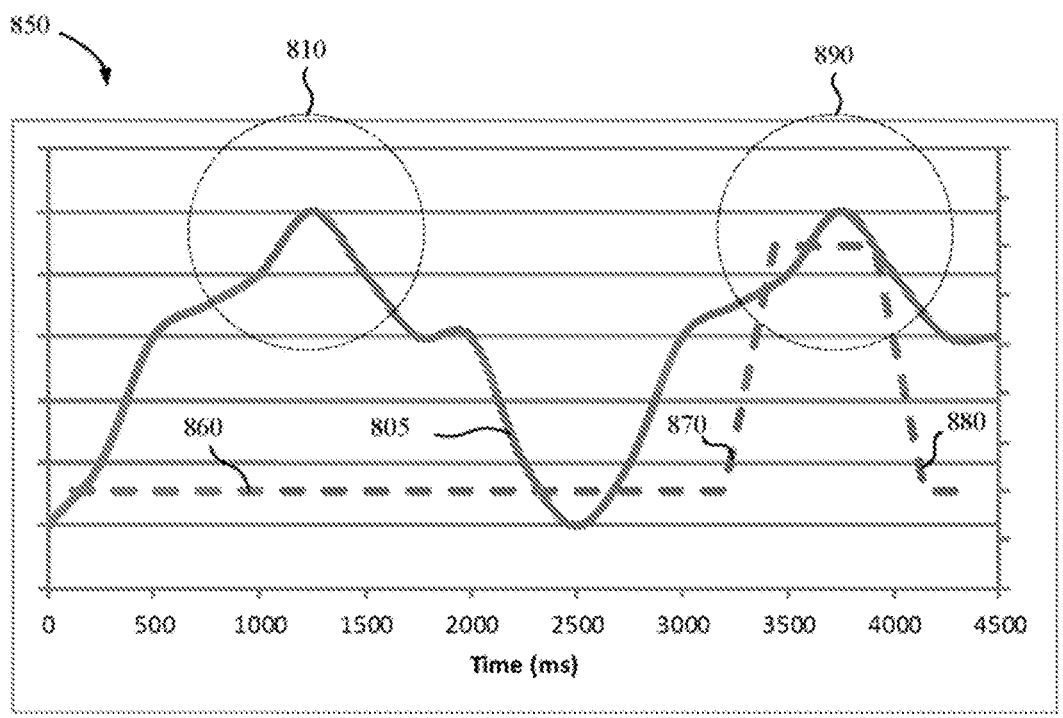
FIG. 8B is a chart illustrating physiological data and an exogenous signal in accordance with some implementations.

As shown in FIGS. 8A and 8B, in some implementations, the physiological data may vary in time and the device 10 may use the physiological data to detect a pattern. In some implementations, the pattern is a change in physiological data from one time to another time, and, in some other implementations, the pattern is series of changes in physiological data over a period of time. Based on detecting the pattern, the device 10 may identify an interest or intent of the user 25 to interact with the object 20 and may adjust the visual characteristic 30 to further identify the interest or intent of the user 25. For example, an intent of a user 25 to select an object 20 may be identified by detecting a pattern in the user's pupillary response, a visual characteristic 30 associated with the object 20 may be adjusted (e.g., changing the object's background from blue to green), and the user's pupillary response to the adjusted visual characteristic 30 may be used to confirm the user's intent to select the object 20. Moreover, the device 10 may identify a pattern associated with an interaction of the user 25 with the object 20 and the visual characteristic 30 may be adjusted in order to better facilitate future identification of the pattern associated with the interaction of the user 25 with the object 20.

FIG. 8A is a chart 800 illustrating detection of a pattern of physiological data. Chart 800 illustrates a time-varying pattern 805 of physiological data, for example, an amount of pupil dilation (y-axis) over time (x-axis). Based on the displayed visual characteristic 30 associated with the object 20, the pattern 805 may include a peak pattern 810 that may be interpreted by device 10 as an indication of an interest or intent of the user 25 in the object 20. In some implementations, the device 10 utilizes a model trained to determine that the peak pattern 810 indicates that the user 25 is involuntarily signaling interest or intent of the user 25 during the time of the peak pattern 810, e.g., based on something the user is looking at or otherwise experiencing during that time period.

In some implementations, the device 10 utilizes a training or calibration sequence to adapt to the specific physiological characteristics of a particular user 25. In some implementations, the device 10 presents the user 25 with a training scenario in which the user 25 is instructed to interact with on-screen items (e.g., object 20). By providing the user 25 with a known intent or area of interest (e.g., via instructions), the device 10 may record the user's physiological data (e.g., pupillary response) and identify a pattern associated with the user's intent or interest 40. In some implementations, the device 10 changes a visual characteristic 30 associated with the object 20 in order to further adapt to the unique physiological characteristics of the user 25. For example, the device 10 could direct a user to mentally select the button in the center of the screen on the count of three and record the user's physiological data 45 to identify a pattern associated with the user's intent or interest 40. Moreover, the device 10 may change or alter a visual characteristic associated with the button in order to identify a pattern associated with the user's physiological response to the altered visual characteristic. In some implementations, the pattern associated with the physiological response of the user 25 is stored in a user profile associated with the user and the user profile can be updated or recalibrated at any time in the future. For example, the user profile could automatically be modified over time during a user experience to provide a more personalized user experience.

In some implementations, a machine learning model (e.g., a trained neural network) is applied to identify patterns in physiological data, including identification of physiological responses to a visual characteristic 30 associated with an object 20.

Moreover, the machine learning model may be used to match the patterns with learned patterns corresponding to indications of interest or intent of the user 25 to interact with the object 20. In some implementations, the device 10 may learn patterns specific to the particular user 25. For example, the device 10 may learn from determining that peak pattern 810 represents an indication of interest or intent of the user 25 in response to a particular visual characteristic 30 and use this information to subsequently identify the similar peak pattern 820 as another indication of interest or intent of the user 25. Such learning can take into account the user's relative interactions with multiple visual characteristics 30, in order to further adjust the visual characteristic 30 and enhance the user's physiological response.

FIG. 8B is a chart 850 illustrating physiological data (e.g., based on measured pupil dilation) and an exogenous signal 860 (e.g., a measure of ambient light at the device 10). The exogenous signal 860 corresponds to a measure of any factor or factors that could influence the physiological data. For example, the amount of ambient light at the device 10 may result in changes to the amount of dilation of the user's eyes, e.g., a decrease in ambient light may result in more dilation of the eyes, etc.

In some implementations, the physiological data is adjusted or otherwise interpreted based on the exogenous signal 860. For example, the peak pattern 810 corresponding to a dilation of the user's eyes may be preliminarily interpreted as an indication of a user with respect to the object given the visual characteristic. Since the exogenous data 860 is level during the time period of peak 810 (e.g., indicating a constant ambient light level), the determination that the dilation should be interpreted as an indication of intent or interest is accepted.

In contrast, the peak pattern 890 corresponding to a dilation of the user's eyes may similarly be preliminarily interpreted as an indication of intent or interest but this determination may be rejected. In this example, the exogenous signal 860 indicates an increase 870 followed by a decrease 880 during the same time period as the peak pattern 890. Thus, the exogenous signal could correspond to an exogenous factor (rather than an interest or intent of the user 25) that caused the peak pattern 890. Accordingly, the device 10 may reject the preliminarily interpretation of peak pattern 890 as an indication of intent or interest. In some implementations, a model is used to account for exogenous signals, e.g., the model is trained to interpret patterns in physiological data that occur during the same time periods as patterns in exogenous signals.

In some implementations, exogenous signals corresponding to pupil diameter changes result from ambient light changes, chromatic changes, accommodation of the eye, content lighting changes, cyclical pupil dilations, a change in ambient noise, or change in motion of the device. For example, an increase in ambient light may correspond to a decreased pupil diameter. Likewise, chromatic changes or changes in content lighting may correspond to increases or decreases in pupil diameter. Moreover, exogenous signals may also be related to the use of drugs or medications. For example, opiates or opioids may be associated with a narrowing of the pupil and cocaine or amphetamines may be associated with a widening of the pupil. In some implementations, based on pupillary response, the device 10 detects patterns that correspond to one or more exogenous factors, for example, based on learning such patterns using a machine learning model. The device 10 may distinguish patterns of physiological data that correspond to interest or intent from patterns of physiological data that correspond to exogenous factors, for example, based on learning such distinctions using a machine learning model.

In some implementations, the device 10 detects the location of the eyes 45 of the user 25 and the pupils 50 of the user 25, e.g., by processing and analyzing an image of light (typically infrared and/or a color produced by the red-green-blue additive color model) reflecting from one or both eyes, in order to locate and measure a diameter of the pupils. The reflected light may originate from a light projecting source of the device 10, or any other natural (e.g., sunlight) or artificial (e.g., a lamp) source. Using techniques such as detecting pupil center and corneal reflections (PCCR), the device 10 may process and analyze an image of light reflecting from an element of the eye 45, including the pupil 50, in order to determine the diameter of the pupil 50. Additionally, the device 10 may process light (e.g., from an illumination source on the device or elsewhere) reflected off the eye 45 of the user 25 as a glint.

In some implementations, the location and features of the head 27 of the user 25 (e.g., an edge of the eye, a nose or a nostril) are extracted by the device 10 and used in finding coarse location coordinates of the eyes 45 of the user 25, thus simplifying the determination of precise eye 45 features (e.g., position, gaze direction, etc.) and making the pupil diameter 55 measurement more reliable and robust. Furthermore, the device 10 may readily combine the 3D location of parts of the head 27 with gaze angle information obtained via eye part image analysis in order to identify a given on-screen object at which the user 25 is looking at any given time. In some implementations, the use of 3D mapping in conjunction with gaze tracking allows the user 25 to move their head 27 and eyes 45 freely while reducing or eliminating the need to actively track the head 27 using sensors or emitters on the head 27.

By tracking the eyes 45, some implementations reduce the need to re-calibrate the user 25 after the user 25 moves their head 27. In some implementations, the device 10 uses depth information to track the pupil's 50 movement, thereby enabling a reliable present pupil diameter 55 to be calculated based on a single calibration of user 25. Utilizing techniques such as pupil-center-corneal reflection (PCCR), pupil tracking, and pupil shape, the device 10 may calculate the pupil diameter 55, as well as a gaze angle of the eye 45 from a fixed point of the head 27, and use the location information of the head 27 in order to re-calculate the gaze angle. In addition to reduced recalibrations, further benefits of tracking the head 27 may include reducing the number of light projecting sources and reducing the number of cameras used to track the eye 45.

Because, in some implementations, user intention is automatically determined based on the eyes 45 of the user 25, selections and other interactions are facilitated without necessarily requiring the user 25 to take action on a physical input device. For example, conventional methods for navigating through user interfaces may be improved upon by providing the device 10 with faster, more efficient methods and interfaces for navigating through user interfaces (e.g., object 20 may be a selectable button of a user interface). Moreover, such methods and interfaces may reduce the cognitive burden on a user 25 and produce a more efficient human-machine interface. For battery-operated computing devices, such methods and interfaces may conserve power and increase the time between battery charges. Moreover, some implementations enhance the navigation of user interfaces based on detecting patterns associated with physiological data.

In accordance with some implementations, a user interface having one or more selectable objects is displayed on a screen of the device 10 and the interest or intent of the user 25 is associated with one of the selectable objects. Moreover, in some implementations, the interest or intent of the user 25 is associated with selecting one of the selectable objects. In some implementations, the device 10 collects physiological data corresponding to an interest or intent of the user to interact with an object 20. Moreover, the device 10 may then enhance a visual characteristic 30 associated with the object 20.

In some implementations, a gesture is received by the device 10 as voluntary data, e.g., behavior over which the user 25 has control. For example, voluntary data may be received based on the user's voice inputs, hand gestures, touch input, keystrokes, etc. In some implementations, the interest or intent of the user to interact with the object 20 is associated with multiple types of input (e.g., multimodal) communicated with the device 10 by the user 25. For example, more than one low-commitment voluntary interactions may, in combination, be associated with the interest or intent of the user 25.

Computing devices are provided with faster, more efficient methods and interfaces for navigating through user interfaces, thereby increasing the effectiveness, efficiency, and user satisfaction with such devices. Such methods and interfaces may complement or replace conventional methods for navigating through user interfaces.

In some implementations, the device 10 uses a detected pattern of physiological data to control a function of the device 10. In some implementations, the device 10 identifies a particular object 20 presented on the display 15 of the device (e.g. at a position in the direction of the user's gaze) and changes a state of the object 20 responsively based on the identified interest or intent of the user 25.

In some implementations, changing the state of the given interactive item includes performing an operation associated with the given interactive item. For example, interactive items may include menu choices that the user 25 can select to present specific content (e.g., a movie or a television show) on the display 15. In some implementations, the device 10 changes the state of a given interactive item by directing input received from the user 25 to the given interactive item. In some implementations, the device 10 identifies the given interactive item based on other data and interact with the interactive item based on the identified user interest or intent. For example if the user 25 is gazing at a selectable button, the device 10 may identify the selectable button based on the user's gaze and then select the selectable button based on the identified user interest or intent.

In some implementations, the device 10 identifies an object 20 presented on the display 15 of the device 10 at a position in the direction of the user's gaze. Moreover, the device 10 may change a state of the visual characteristic 30 associated with the object 20 responsively to a spoken verbal command received from the user 25 in combination with the identified interest or intent of the user 25. For example, the object 20 may be an icon associated with a software application, and the user 25 may gaze at the icon, say the word "select" to choose the application, and a highlighting effect may be applied to the icon. The device 10 may then use further physiological data in response to the visual characteristic 30 to further identify interest or intent of the user 25 as a confirmation of the user's verbal command. In some implementations, the device 10 is configured to identify a given interactive item responsive to the direction of the user's gaze, and to manipulate the given interactive item responsively to physiological data (e.g., pupillary data). The device 10 may then confirm the direction of the user's gaze based on further identifying user interest or intent with physiological data. In some implementations, the device 10 removes an interactive item or object based on the identified interest or intent. In other implementations, the device 10 automatically captures images of the content at times when the an interest or intent of the user 25 is determined.

In some implementations, the device 10 is configured to provide a progressive interface. The progressive interface may aid the usability of voluntary inputs from the user 25 in combination with, or supported by, the physiological data (e.g., one or more involuntary characteristics of the user 25). For example, by adjusting the visual characteristic 30, the device 10 may provide progressive feedback to the user 25 regarding an identified interest or intent of the user 25 while simultaneously eliciting an increased physiological response to the adjustment of the visual characteristic 30. In some implementations, the device 10 begins a low-commitment interaction with the user 25 in response to detecting a pattern of physiological data or in response to receiving voluntary user input. For example, in response to one or more lower-confidence detections of user interest or intent to interact with the object 20, the device 10 may modify or adjust a visual characteristic associated with the object 20 (e.g., highlighting the object with an optimal color). In some implementations, the modification of the visual characteristic 30 may direct the user 25 to progressively perform higher commitment actions to confirm the user interest or intent to interact with the object 20. For example, the device 10 may act on or delete an item in response to further input from the user 25.

As a power saving feature, the device 10 may detect when the user 25 is not looking at the display and the device 10 may activate power saving techniques, e.g., disabling physiological sensors when the user 25 looks away for more than some threshold period of time. Furthermore, in some implementations, the device 10 dims or darkens the display (e.g., decrease the brightness) entirely when the user 25 is not looking at the display. When the user 25 looks back toward the display, the device 10 may deactivate the power saving techniques. In some implementations, the device 10 tracks a physiological attribute using a first sensor and then activates a second sensor to obtain the physiological data based on the tracking. For example, the device 10 may use a camera to identify that the user 25 is looking in the direction of the device 10 and then activate an eye sensor when it is determined that the user 25 is looking in the direction of the device 10.

In some implementations, a combination of determining user intent and an input device 10 is used to create an interactive user interface that utilizes the input device 10 to identify an on-screen interactive item and determine the user's interest or intent in interacting with the on-screen interactive item. For example, a user 25 may use a mouse to select an on-screen interactive item based on the user's determined interest or intent, e.g., a "mouse click" type event triggered by determining the user's interest or intent rather than a mouse click. In some implementations, a combination of determining user intent and gaze tracking is used to create an interactive user interface that can detect which on-screen interactive item the user 25 is looking at (e.g., gaze tracking) and determine the user's interest or intent in interacting with the on-screen interactive item, thereby obviating the need for a mouse and/or a keyboard.

Furthermore, the combination of determining user interest or intent with other modalities, such as gaze tracking, facial gesture detection, 3D mapping/gesture detection and/or voice detection, enables the user 25 to control on-screen objects fully, without the use of a mouse or a touch screen. In this manner, the user 25 can perform a full range of pointing and selection functions, including searching through large numbers of information items and choices. The combined interface modalities may also be used to search and perform control functions within the context of a certain interactive item, such as performing find, cut, copy and paste functions within an open file. In some implementations, the device 10 identifies a first interest, or group of first interests, and then progressively identifies a second interest, or second group of interests, based on the previously identified interest(s).

In some implementations, the device 10 utilizes a training or calibration sequence to adapt to the specific physiological characteristics of a particular user 25. In some implementations, the device 10 presents the user 25 with a training scenario in which the user 25 is instructed to interact with on-screen items. By providing the user 25 with one or more known visual characteristics 30 associated with known objects 20, the device 10 may record the user's physiological data and identify a pattern associated with the user's intent or interest. For example, the device 10 could direct a user 25 to focus on a red button in the center of the display 15 on the count of three and record the user's physiological data to identify a pattern associated with the user's intent or interest as it relates to the green visual characteristic 30. The device 10 could then repeat the same process with a number of other differently colored buttons in order to identify a color that elicits the highest physiological response for the user 25. In some implementations, the pattern associated with the user's intent or interest, physiological data associated with particular visual characteristics 30, or a ranking or analysis of particular visual characteristics 30 in relation to the user 25 are stored in a user profile associated with the user and the user profile can be updated or recalibrated at any time in the future. For example, the user profile could automatically be modified over time during a user experience to provide a more personalized user experience.

Figure 9:
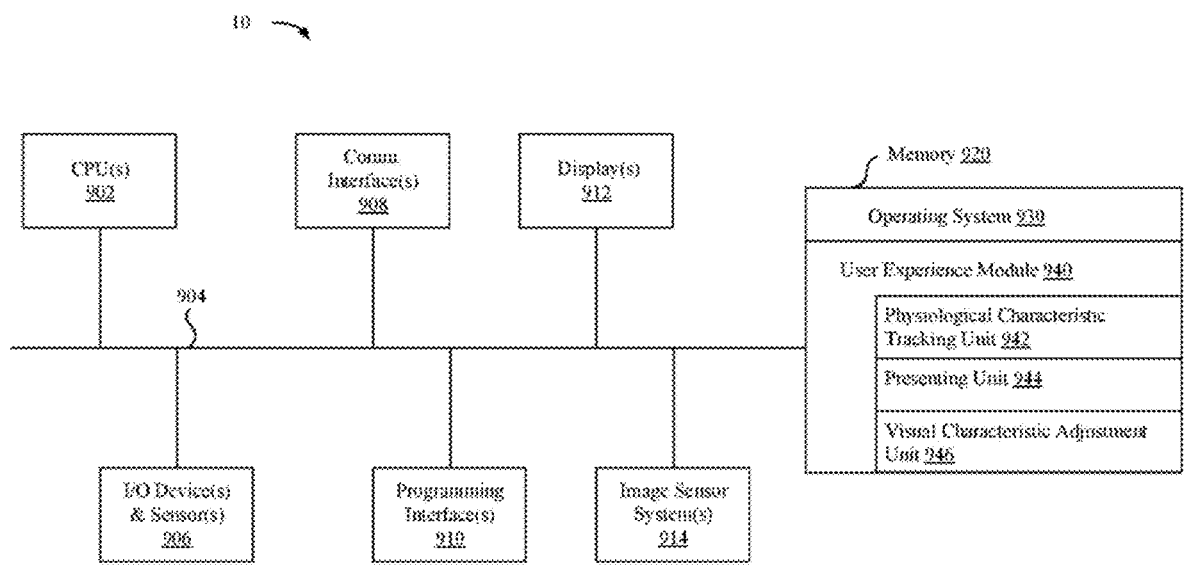
FIG. 9 is a block diagram illustrating device components of an exemplary device according to some implementations.

FIG. 9 is a block diagram of an example of a device 10 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 10 includes one or more processing units 902 (e.g., microprocessors, ASICs, FPGAs, GPUs, CPUs, processing cores, and/or the like), one or more input/output (I/O) devices and sensors 906, one or more communication interfaces 908 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 910, one or more displays 912, one or more interior and/or exterior facing image sensor systems 914, a memory 920, and one or more communication buses 904 for interconnecting these and various other components.

In some implementations, the one or more communication buses 904 include circuitry that interconnects and controls communications between system components. In some implementations, the one or more I/O devices and sensors 906 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 912 are configured to present a user experience to the user 25. In some implementations, the one or more displays 912 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), microelectromechanical system (MEMS), a retinal projection system, and/or the like display types. In some implementations, the one or more displays 912 correspond to diffractive, reflective, polarized, holographic, etc. waveguide displays. In one example, the device 10 includes a single display. In another example, the device 10 includes a display for each eye of the user 25, e.g., an HMD. In some implementations, the one or more displays 912 are capable of presenting MR content, including VR or AR content.

In some implementations, the one or more image sensor systems 914 are configured to obtain image data that corresponds to at least a portion of the face of the user 25 that includes the eyes of the user 25. For example, the one or more image sensor systems 914 include one or more RGB camera (e.g., with a complimentary metal-oxide-semiconductor (CMOS) image sensor or a charge-coupled device (CCD) image sensor), monochrome camera, IR camera, event-based camera, and/or the like. In various implementations, the one or more image sensor systems 914 further include illumination sources that emit light upon the portion of the face of the user 25, such as a flash or a glint source.

The memory 920 includes high-speed random-access memory, such as DRAM, SRAM, DDR RAM, or other random-access solid-state memory devices. In some implementations, the memory 920 includes non-volatile memory, such as one or more magnetic disk storage devices, optical disk storage devices, flash memory devices, or other non-volatile solid-state storage devices. The memory 920 optionally includes one or more storage devices remotely located from the one or more processing units 902. The memory 920 comprises a non-transitory computer readable storage medium. In some implementations, the memory 920 or the non-transitory computer readable storage medium of the memory 920 stores the following programs, modules and data structures, or a subset thereof including an optional operating system 920 and a user experience module 940.

The operating system 930 includes procedures for handling various basic system services and for performing hardware dependent tasks. In some implementations, the user experience module 940 is configured to present a user experience that utilizes physiological data to identify an interest or intent of the user 25 via context aware dynamic distortion correction to the user 25 via the one or more input/output (I/O) devices and sensors 906. To that end, in various implementations, the user experience module 940 includes a physiological characteristic tracking unit 942, a presenting unit 944, and a visual characteristic adjustment unit 946.

In some implementations, the physiological characteristic tracking unit 942 is configured to obtain physiological data (e.g., pupil dilation, electroencephalography, etc.) and to use the obtained physiological data to identify patterns of physiological data. To that end, in various implementations, the physiological characteristic tracking unit 942 includes instructions and/or logic therefor, and heuristics and metadata therefor.

In some implementations, the presenting unit 944 is configured to present an object with an associated visual characteristic via the one or more displays 912. To that end, in various implementations, the presenting unit 944 includes instructions and/or logic therefor, and heuristics and metadata therefor.

In some implementations, the visual characteristic adjustment unit 946 is configured to adjust the visual characteristic to enhance a physiological response (e.g., pupillary response) to the adjusted visual characteristic. To that end, in various implementations, the visual characteristic adjustment unit 946 includes instructions and/or logic therefor, and heuristics and metadata therefor.

Although the physiological characteristic tracking unit 942, the presenting unit 944, and the visual characteristic adjustment unit 946 are shown as residing on a single device (e.g., the device 10), it should be understood that in other implementations, any combination of these units may be located in separate computing devices.

Moreover, FIG. 9 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 7 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 10:
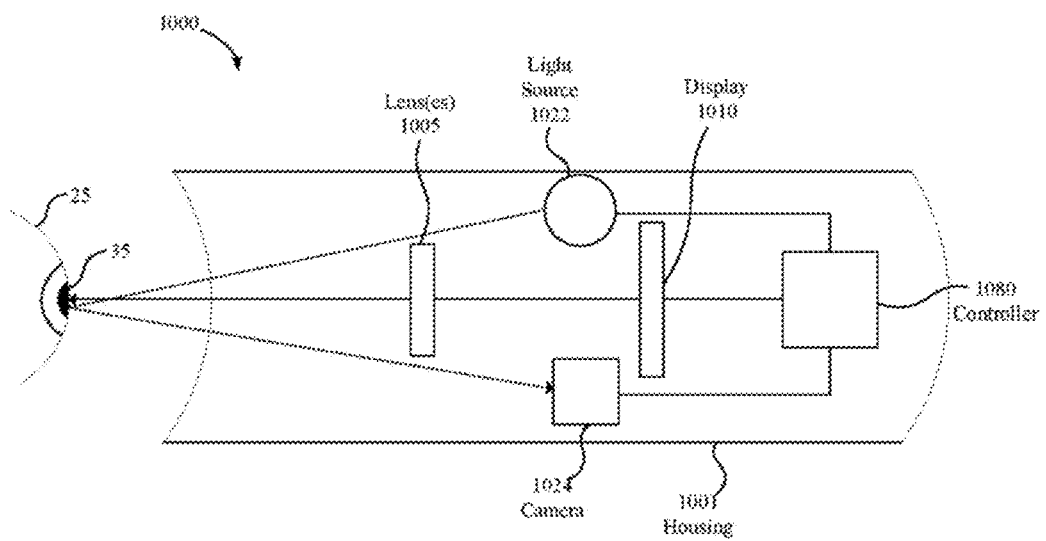
FIG. 10 is a block diagram of an example head-mounted device (HMD) in accordance with some implementations.

FIG. 10 illustrates a block diagram of an exemplary head-mounted device 1000 in accordance with some implementations. The head-mounted device 1000 includes a housing 1001 (or enclosure) that houses various components of the head-mounted device 1000. The housing 1001 includes (or is coupled to) an eye pad (not shown) disposed at a proximal (to the user 25) end of the housing 1001. In various implementations, the eye pad is a plastic or rubber piece that comfortably and snugly keeps the head-mounted device 1000 in the proper position on the face of the user 25 (e.g., surrounding the eye of the user 25).

The housing 1001 houses a display 810 that displays an image, emitting light towards or onto the eye of a user 25. In various implementations, the display 1010 emits the light through an eyepiece having one or more lenses 1005 that refracts the light emitted by the display 1010, making the display appear to the user 25 to be at a virtual distance farther than the actual distance from the eye to the display 1010. For the user 25 to be able to focus on the display 1010, in various implementations, the virtual distance is at least greater than a minimum focal distance of the eye (e.g., 7 cm). Further, in order to provide a better user experience, in various implementations, the virtual distance is greater than 1 meter.

The housing 1001 also houses a tracking system including one or more light sources 1022, camera 1024, and a controller 1080. The one or more light sources 1022 emit light onto the eye of the user 25 that reflects as a light pattern (e.g., a circle of glints) that can be detected by the camera 1024. Based on the light pattern, the controller 880 can determine an eye tracking characteristic of the user 25. For example, the controller 1080 can determine a gaze direction and/or a blinking state (eyes open or eyes closed) of the user 25. As another example, the controller 1080 can determine a pupil center, a pupil size, or a point of regard. Thus, in various implementations, the light is emitted by the one or more light sources 1022, reflects off the eye of the user 25, and is detected by the camera 1024. In various implementations, the light from the eye of the user 25 is reflected off a hot mirror or passed through an eyepiece before reaching the camera 1024.

The display 1010 emits light in a first wavelength range and the one or more light sources 1022 emit light in a second wavelength range. Similarly, the camera 1024 detects light in the second wavelength range. In various implementations, the first wavelength range is a visible wavelength range (e.g., a wavelength range within the visible spectrum of approximately 400-700 nm) and the second wavelength range is a near-infrared wavelength range (e.g., a wavelength range within the near-infrared spectrum of approximately 700-1400 nm).

In various implementations, eye tracking (or, in particular, a determined gaze direction) is used to enable user interaction (e.g., the user 25 selects an option on the display 1010 by looking at it), provide foveated rendering (e.g., present a higher resolution in an area of the display 1010 the user 25 is looking at and a lower resolution elsewhere on the display 1010), or correct distortions (e.g., for images to be provided on the display 1010).

In various implementations, the one or more light sources 1022 emit light towards the eye of the user 25 which reflects in the form of a plurality of glints.

In various implementations, the camera 1024 is a frame/shutter-based camera that, at a particular point in time or multiple points in time at a frame rate, generates an image of the eye of the user 25. Each image includes a matrix of pixel values corresponding to pixels of the image which correspond to locations of a matrix of light sensors of the camera. In implementations, each image is used to measure or track pupil dilation by measuring a change of the pixel intensities associated with one or both of a user's pupils.

In various implementations, the camera 1024 is an event camera comprising a plurality of light sensors (e.g., a matrix of light sensors) at a plurality of respective locations that, in response to a particular light sensor detecting a change in intensity of light, generates an event message indicating a particular location of the particular light sensor.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

As described above, one aspect of the present technology is the gathering and use of physiological data to improve a user's experience of an electronic device with respect to interacting with electronic content. The present disclosure contemplates that in some instances, this gathered data may include personal information data that uniquely identifies a specific person or can be used to identify interests, traits, or tendencies of a specific person. Such personal information data can include physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to improve interaction and control capabilities of an electronic device. Accordingly, use of such personal information data enables calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information and/or physiological data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying and/or personal information about the user, such as a legal name, username, time and location data, or the like). In this way, other users, hackers, or third parties cannot determine the identity of the user associated with the stored data. In some implementations, a user may access their stored data from a user device that is different than the one used to upload the stored data. In these instances, the user may be required to provide login credentials to access their stored data.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:
at a device comprising a processor, a computer-readable storage medium, a display, and a sensor:
displaying, on the display to a user, a visual characteristic associated with an object;
obtaining, using the sensor, first physiological data associated with a first pupillary response of the user to the visual characteristic;
determining an interest of the user to interact with the object, wherein determining the interest of the user to interact with the object comprises detecting, based on the obtained first physiological data, a pupil dilation pattern by accounting for exogenous signals corresponding to pupil diameter changes;
determining that adjusting the visual characteristic associated with the object will produce pupillary responses greater than the first pupillary response;
in accordance with determining that adjusting the visual characteristic will produce pupillary responses greater than the first pupillary response, adjusting, based on the obtained first physiological data and the determined interest of the user, the visual characteristic to enhance pupillary responses of the user with respect to the adjusted visual characteristic associated with the object; and
displaying the object with the adjusted visual characteristic.

2. The method of claim 1 further comprising:
obtaining second physiological data associated with a second pupillary response of the user to the adjusted visual characteristic; and
determining, based on the obtained second physiological data, an intention of the user to interact with the object.

3. The method of claim 1, wherein the first physiological data comprises a pupil diameter of an eye of the user or a change in the pupil diameter of the eye of the user.

4. The method of claim 1, wherein detecting the pupil dilation pattern comprises obtaining pupil dilation data corresponding to each of multiple variations of the visual characteristic, and wherein adjusting the visual characteristic comprises selecting a variation of the variations to adjust the visual characteristic based on the pupil dilation data.

5. The method of claim 1, wherein accounting for the exogenous signals corresponding to the pupil diameter is based on determining changes in the pupil dilation pattern resulting from at least one of: ambient light changes, chromatic changes, accommodation of an eye of the user, content lighting changes, cyclical pupil dilations, a change in ambient noise, motion of the device, a luminance of an environment of the user, a cognitive load, and a user caffeine intake.

6. The method of claim 1, wherein determining the interest of the user to interact with the object includes applying a machine learning technique trained to identify patterns in physiological data corresponding to user intentions.

7. The method of claim 1, wherein determining the interest of the user to interact with the object comprises identifying at least one of: an intent to execute a movement, make a decision, and select the object at a particular instant in time.

8. The method of claim 1, wherein the device is a handheld device, a laptop, or a desktop, or a head-mounted-device (HMD).

9. The method of claim 1, wherein the visual characteristic is a color attribute of the object, a size of the object, a shape of the object, or an attribute of content proximate to the object.

10. The method of claim 1, wherein the first physiological data is obtained based on identifying an interaction of the user with the displayed object.

11. A system comprising:
a device with a display and a sensor;
a processor; and
a computer-readable storage medium comprising instructions that upon execution by the processor cause the system to perform operations, the operations comprising:
displaying, on the display to a user, a visual characteristic associated with an object;
obtaining, using the sensor, first physiological data associated with a first pupillary response of the user to the visual characteristic;
determining an interest of the user to interact with the object, wherein determining the interest of the user to interact with the object comprises detecting, based on the obtained first physiological data, a pupil dilation pattern by accounting for exogenous signals corresponding to pupil diameter changes;
determining that adjusting the visual characteristic associated with the object will produce pupillary responses greater than the first pupillary response;
in accordance with determining that adjusting the visual characteristic will produce pupillary responses greater than the first pupillary response, adjusting, based on the obtained first physiological data and the determined interest of the user, the visual characteristic to enhance pupillary responses of the user with respect to the adjusted visual characteristic associated with the object; and
displaying the object with the adjusted visual characteristic.

12. The system of claim 11, wherein the operations further comprise:
obtaining second physiological data associated with a second pupillary response of the user to the adjusted visual characteristic; and
determining, based on the obtained second physiological data, an intention of the user to interact with the object.

13. The system of claim 11, wherein the first physiological data comprises a pupil diameter of an eye of the user or a change in the pupil diameter of the eye of the user.

14. The system of claim 11, wherein detecting the pupil dilation pattern comprises obtaining pupil dilation data corresponding to each of multiple variations of the visual characteristic, and wherein adjusting the visual characteristic comprises selecting a variation of the variations to adjust the visual characteristic based on the pupil dilation data, of the variations to adjust the visual characteristic based on the pupil dilation data.

15. The system of claim 11, wherein accounting for the exogenous signals corresponding to the pupil diameter is based on determining changes in the pupil dilation pattern resulting from at least one of: ambient light changes, chromatic changes, accommodation of an eye of the user, content lighting changes, cyclical pupil dilations, a change in ambient noise, motion of the device, a luminance of an environment of the user, a cognitive load, and a user caffeine intake.

16. The system of claim 11, wherein determining the interest of the user to interact with the object includes applying a machine learning technique trained to identify patterns in physiological data corresponding to user intentions.

17. The system of claim 11, wherein determining the interest of the user to interact with the object comprises identifying at least one of: an intent to execute a movement, make a decision, and select the object at a particular instant in time.

18. A non-transitory computer-readable storage medium storing program instructions that are computer-executable to perform operations comprising:
displaying, by a device including a display and a sensor, a visual characteristic associated with an object on the display to a user;
obtaining, using the sensor, first physiological data associated with a first pupillary response of the user to the visual characteristic;
determining an interest of the user to interact with the object, wherein determining the interest of the user to interact with the object comprises detecting, based on the obtained first physiological data, a pupil dilation pattern by accounting for exogenous signals corresponding to pupil diameter changes;
determining that adjusting the visual characteristic associated with the object will produce pupillary responses greater than the first pupillary response;
in accordance with determining that adjusting the visual characteristic will produce pupillary responses greater than the first pupillary response, adjusting, based on the obtained first physiological data and the determined interest of the user, the visual characteristic to enhance pupillary responses of the user with respect to the adjusted visual characteristic associated with the object; and
displaying the object with the adjusted visual characteristic.

* * * * *